United States Patent
Ryu et al.

(10) Patent No.: US 7,964,584 B2
(45) Date of Patent: Jun. 21, 2011

(54) METHOD OF TREATING OR PREVENTING OSTEOPOROSIS COMPRISING ADMINISTERING TO A PATIENT IN NEED THEREOF AN EFFECTIVE AMOUNT OF PHARMACEUTICAL COMPOSITION COMPRISING BENZAMIDINE DERIVATIVES OR THEIR SALTS, AND ALENDRONIC ACID OR ITS SALT

(75) Inventors: Jei Man Ryu, Gyeonggi-do (KR); Jin Soo Lee, Gyeonggi-do (KR); Jae Hoon Park, Seoul (KR); Yun-Ha Hwang, Gyeonggi-do (KR); Duk Kyun Chung, Seoul (KR)

(73) Assignee: Dong Wha Pharmaceutical Co., Ltd., Seoul (KR)

( * ) Notice: Subject to any disclaimer, the term of this patent is extended or adjusted under 35 U.S.C. 154(b) by 13 days.

(21) Appl. No.: 12/533,537

(22) Filed: Jul. 31, 2009

(65) Prior Publication Data
US 2010/0029595 A1     Feb. 4, 2010

Related U.S. Application Data

(60) Provisional application No. 61/085,573, filed on Aug. 1, 2008.

(51) Int. Cl.
*A61K 31/66*     (2006.01)
*A61K 31/425*    (2006.01)

(52) U.S. Cl. ...................................... 514/114; 514/365

(58) Field of Classification Search .................. 514/114, 514/365
See application file for complete search history.

(56) References Cited

U.S. PATENT DOCUMENTS

| | | | |
|---|---|---|---|
| 4,407,761 A | 10/1983 | Blum et al. | |
| 4,621,077 A | 11/1986 | Rosini et al. | |
| 4,705,651 A | 11/1987 | Staibano | |
| 5,039,819 A | 8/1991 | Kieczykowski | |
| 5,159,108 A | 10/1992 | Kieczykowski | |
| 2010/0029596 A1 * | 2/2010 | Ryu et al. ...................... | 514/108 |

FOREIGN PATENT DOCUMENTS

| | | |
|---|---|---|
| KR | 2003-0008654 A | 1/2003 |
| WO | WO-01/28564 A1 | 4/2001 |

OTHER PUBLICATIONS

Andrew S Neviaser et al, "Low-Energy Femoral Shaft Fractures Associated With Alendronate Use", Journal of Orthopedic Trauma, 2008, 22(5), 346-350.
Lindsay et al, "Addition of Alendronate to Ongoing Hormone Replacement Therapy in the Treatment of Osteoporosis: A Randomized, Controlled Clinical Trail", J. Clin Endocrinol. Metab. 84, 3073-3081 (1999).
Johnell et al, "Additive Effects of Raloxifene and Alendronate on Bone Density and Biochemical Markeser of Bone Remodeling in Postmenopausal Women with Osteoporosis", J. Clin. Endocrinol. Metab. 87, 985-992 (2002).
Greenspan et al, "Combination Therapy With Hormone Replacement and Alendronate for Prevention of Bone Loss in Elderly Women: A Randomized Controlled Trail", JAMA, 289, 2525-2533 (2003).
Black et al, "The Effects of Parathyroid Hormone and Alendronate Alone or in Combination in Postmenopausal Osteoporosis", N. Eng. J. Med. 349, 1207-1215, (2003).
Finkelstein et al, "The Effects of Parathyroid Hormone Alendronate, or Both in Men with Osteoporosis", N. Eng. J. Med. 349, 1216-1226, (2003).
Lee, Sung-Eun, "Design, Synthesis, and Evaluation of functional Molecules for the Treatment of LTB4 Related Disease and Electroluminescent Device", Synthesis and Biological Activity of Natural Products and Designed New Hybrid Compounds for the Treatment of LTB4 Related Disease, Busan National University, a thesis for a Ph. D degree, 1999. 8.

* cited by examiner

*Primary Examiner* — Raymond J Henley, III
(74) *Attorney, Agent, or Firm* — Arent Fox LLP

(57) ABSTRACT

The present invention relates to a pharmaceutical composition for preventing and treating osteoporosis, comprising N-hydroxy-4-{5-[4-(5-isopropyl-2-methyl-1,3-thiazol-4-yl)phenoxy]pentoxy}benzamidine, 4-{5-[4-(5-isopropyl-2-methyl-1,3-thiazol-4-yl)phenoxy]pentoxy}benzamidine, or salts thereof, and alendronic acid or a salt thereof.
As a prophylactic or therapeutic composition for osteoporosis, the combination treatment of N-hydroxy-4-{5-[4-(5-isopropyl-2-methyl-1,3-thiazol-4-yl)phenoxy]pentoxy}benzamidine, 4-{5-[4-(5-isopropyl-2-methyl-1,3-thiazol-4-yl)phenoxy]pentoxy}-benzamidine, or salts thereof and alendronic acid or a salt thereof exhibits excellent inhibitory effect on osteoclast differentiation, as compared to each individual treatment, thereby being useful for the prevention or treatment of osteoporosis.

6 Claims, 3 Drawing Sheets

[Fig. 1]
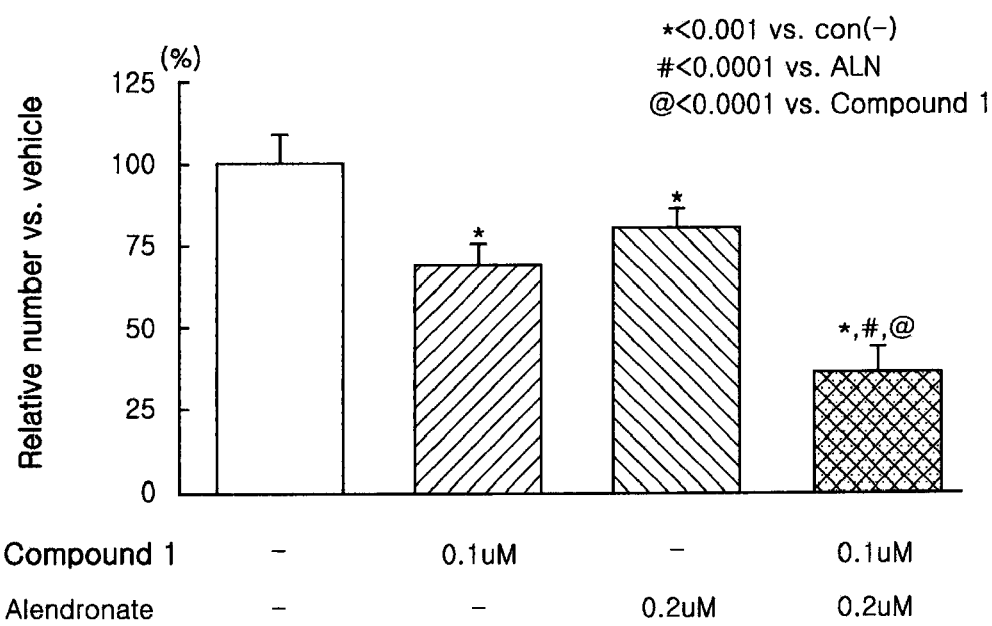

[Fig. 2]
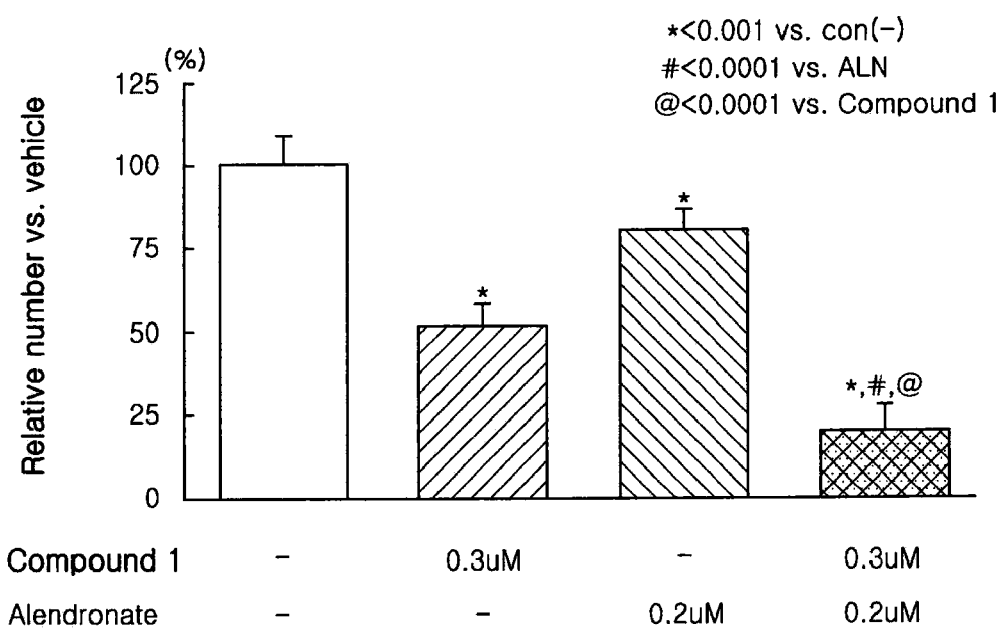

[Fig. 3]
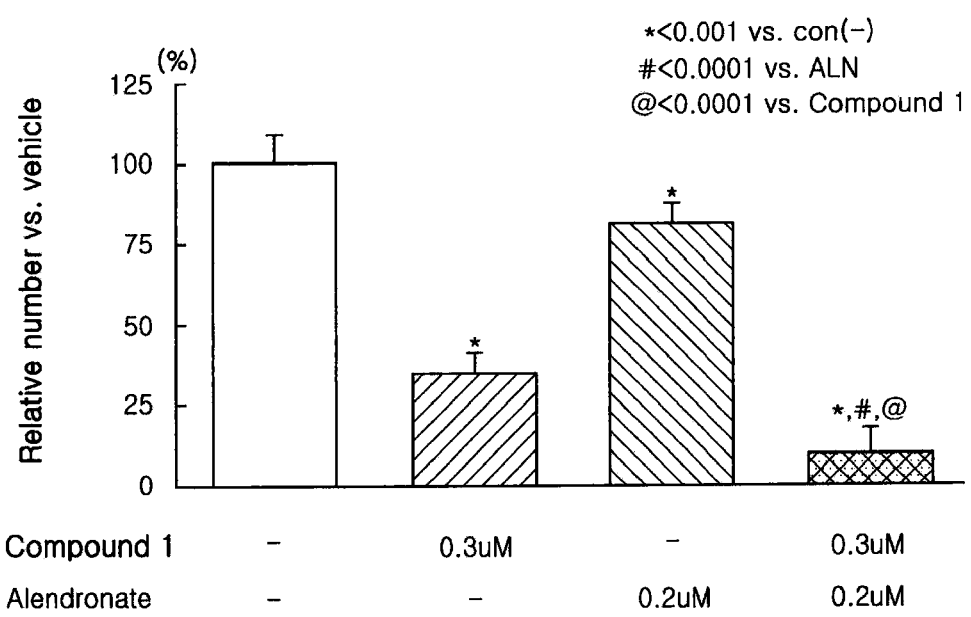

METHOD OF TREATING OR PREVENTING OSTEOPOROSIS COMPRISING ADMINISTERING TO A PATIENT IN NEED THEREOF AN EFFECTIVE AMOUNT OF PHARMACEUTICAL COMPOSITION COMPRISING BENZAMIDINE DERIVATIVES OR THEIR SALTS, AND ALENDRONIC ACID OR ITS SALT

CROSS-REFERENCE TO RELATED APPLICATION

This application claims priority to U.S. Provisional Patent Application No. 61/085,573, filed on Aug. 1, 2008, the contents of which are incorporated herein by reference in their entirety.

BACKGROUND OF THE INVENTION

1. Field of the Invention

The present invention relates to a method of treating or preventing osteoporosis comprising administering to a patient in need thereof an effective amount of pharmaceutical composition comprising N-hydroxy-4-{5-[4-(5-isopropyl-2-methyl-1,3-thiazol-4-yl)phenoxy]pentoxy}benzamidine, 4-{5-[4-(5-isopropyl-2-methyl-1,3-thiazol-4-yl)phenoxy]pentoxy}benzamidine, or salts thereof, and alendronic acid or a salt thereof.

2. Description of the Related Art

Bone is a supporting material for the body's framework and serves to conserve the necessary bone mass and structure. Bone also functions as a reservoir of calcium ($Ca^{2+}$) or the like, and plays an important role in maintaining the calcium level in the blood. The bone is in a dynamic steady state, 'bone remodeling' which maintains a delicate balance by continuously performing both bone resorption and bone formation. Bone remodeling is a complex process involving bone formation by osteoblasts and bone resorption and degradation by osteoclasts, and maintains a physiological and metabolic balance. However, the balance between bone resorption and bone formation is disrupted by various factors and diseases, leading to osteoporosis.

Osteoporosis is a bone disease, which results from a disturbance in the balance between bone resorption and bone formation, caused by having a higher degree of bone resorption relative to that of bone formation. This disease frequently occurs in middle-aged or elderly women. Osteoporosis reduces calcification of bone tissues, and decreases the level of the compact substances in the bone, which broadens the marrow cavity, and causes reduction in bone density or bone mass, resulting in decrease in bone strength. Consequently, as osteoporosis progresses, bone becomes brittle, and bone fracture may easily occur even with a small impact.

Bone fracture is associated with an increased mortality rate of patients with osteoporosis, and also causes serious problems such as negative impact on patients' quality of life. Thus, various strategies have been established to produce drugs capable of increasing of bone density and decreasing of the risk of bone fracture.

To date, bisphosphonate (alendronate, etidronate), hormones (raloxifen), vitamin D, calcitonin, calcium agents, or the like have been used as an anti-osteoporotic agent, and Forteo™, a form of parathyroid hormone responsible for bone formation, is currently used to treat advanced osteoporosis. However, they are known to have adverse effects. Specifically, hormone agents must be administered throughout patient's life, and in the case of long-term administration, side effects such as breast cancer, uterus cancer, gallstones and thrombosis may be induced. Vitamin D agents are expensive and show little efficacy, and calcitonin agents are also very expensive and difficult to administer. Calcium agents have few side effects, but their effects are restricted to the prevention of osteoporosis, not the treatment itself. Forteo™, a commercially available parathyroid hormone, has an advantage in that it stimulates bone formation, whereas the known drugs are restricted to the prevention of bone resorption. However, Forteo™ should be given as a daily injection for a long period of time, and may increase the risk of osteosarcoma. Its application is also restricted due to the high price.

A bisphosphonate drug, alendronate, represented by the following Formula, has been widely used for the treatment of osteoporosis, and shown to increase bone density and prevent fractures as an inhibitor of bone resorption. Owing to advantages of oral administration and lower cost, it has been widely used in clinical fields for the treatment of calcium metabolic disorders including osteoporosis.

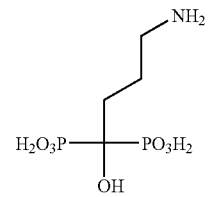

However, bisphosphonate agents show low absorptivity and may induce esophagitis, and thus should be taken with a sufficient amount of water before meals. In addition, patients should wait at least 30 minutes before ingesting other beverage or food, and avoid lying down for a predetermined time following administration. They are also reported to increase the risk of hypocalcemia. Recent studies have suggested problems such as reduction in bone turnover rate due to excessive inhibition of bone resorption, inhibition of bone formation, gastrointestinal disorders and osteonecrosis of the jaw. Furthermore, it is recently reported that its long term administration increases the risk of bone fractures (Andrew S Neviaser et al, *Journal of Othopaedic Trauma*, 2008, 22(5), 346-350).

As described above, the current therapeutic agents for osteoporosis are not those which act on both bone resorption and formation. Accordingly, in order to treat osteoporosis, there is a need for the development of drugs and therapies which lead to balanced increase in the bone mass and improvement of bone quality, and thus reduce the risk of bone fractures.

To overcome the above drawbacks and improve the clinical efficacy, many studies have been made, and recent studies suggested combination therapy of a bone resorption inhibitor and a commercially available parathyroid hormone that stimulates bone formation. The detailed description thereof is as follows.

The combination therapy of alendronate and other bone resorption inhibitor are exemplified by alendronate and estrogen (literature—Lindsay et al, *J. Clin. Endocrinol. Metab.* 84, 3073-3081 (1999)), alendronate and raloxifene (literature—Johnell et al, *J. Clin. Endocrinol. Metab.* 87, 985-992 (2002)), alendronate and HRT (hormone replacement therapy) (literature—Greenspan et al, *JAMA*, 289, 2525-2533 (2003)), and alendronate and calcitriol (WO 01/28564). These studies demonstrated that the combination therapy showed an increase in bone density, compared to their individual administration, but no reduction in the risk of bone fracture. Moreover, problems including reduction in bone turnover rate due to inhibitory effect on bone resorption and inhibition of bone formation still remain, even though there are differences between their mechanisms. Thus, there are needs for considerations and further studies regarding the therapies.

In this regard, there was a trial of combination therapy with a bone formation stimulator, which was intended to reduce inhibitory effect on bone formation and adverse effects of alendronate. Combination therapy of alendronate with a parathyroid hormone is exemplified by two literatures: The effects of parathyroid hormone and alendronate in combination in postmenopausal osteoporosis (literature—Black et al, *N. Eng. J. Med.* 349, 1207-1215, (2003)) and in elderly men with osteoporosis (literature—Finkelstein et al, *N. Eng. J. Med.* 349, 1216-1226, (2003)). However, the literatures did not demonstrate the increase in bone density, compared to their individual administration. In this regard, some researchers suggested the possibility that a strong bone resorption inhibitor, alendronate counteracts the stimulating effect of parathyroid hormone. Subsequently, a sequential administration of two drugs has been tried, but further studies are still needed for a meaningful clinical outcome.

On the other hand, the present inventors have confirmed that the benzamidine derivative, N-hydroxy-4-{5-[4-(5-isopropyl-2-methyl-1,3-thiazol-4-yl)phenoxy]pentoxy}benzamidine and 4-{5-[4-(5-isopropyl-2-methyl-1,3-thiazol-4-yl)phenoxy]pentoxy}benzamidine or salts thereof are very useful as a prophylactic and therapeutic agent for osteoporosis, which is disclosed in Korea Patent No. 454767.

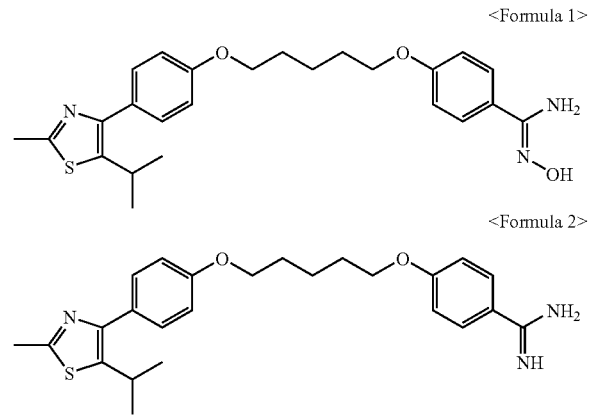

Accordingly, the present inventors have studied that the ingredients of Formulae 1 and 2 being useful for the prevention and treatment of osteoporosis are administered in combination with conventional bone resorption inhibitors, such as bisphosphonate (alendronate), hormones (raloxifen), vitamin D, calcitonin and calcium agents, and bone formation stimulators, and developed a new therapy to offer their benefits without their potential drawbacks.

Consequently, the present inventors have confirmed that N-hydroxy-4-{5-[4-(5-isopropyl-2-methyl-1,3-thiazol-4-yl)phenoxy]pentoxy}benzamidine, 4-{5-[4-(5-isopropyl-2-methyl-1,3-thiazol-4-yl)phenoxy]pentoxy}benzamidine or salts thereof and alendronic acid or a salt thereof capable of being used as a single formulation are administered in combination to provide an excellent pharmaceutical composition for preventing or treating osteoporosis, thereby completing the present invention.

SUMMARY OF THE INVENTION

It is an object of the present invention to provide a pharmaceutical composition for preventing or treating osteoporosis, comprising N-hydroxy-4-{5-[4-(5-isopropyl-2-methyl-1,3-thiazol-4-yl)phenoxy]pentoxy}benzamidine, 4-{5-[4-(5-isopropyl-2-methyl-1,3-thiazol-4-yl)phenoxy]pentoxy}benzamidine or salts thereof, and alendronic acid or a salt thereof, and a method for preventing or treating osteoporosis using the same.

BRIEF DESCRIPTION OF THE DRAWINGS

FIG. 1 is a graph showing the effect of individual or combination treatment of 0.1 μM N-hydroxy-4-{5-[4-(5-isopropyl-2-methyl-1,3-thiazol-4-yl) phenoxy]pentoxy}benzamidine dimethanesulfonate and 0.2 μM alendronic acid on osteoclast differentiation, in which osteoclast differentiation was induced via co-culture of bone marrow cell and osteoblast, the cells were treated with each sample substance singly or simultaneously, and cultured for 7 days, and then TRAP staining was performed to count mature osteoclasts with 6 or more nuclei, expressed as a percentage to a control group.

FIG. 2 is a graph showing the effect of individual or combination treatment of 0.3 μM N-hydroxy-4-{5-[4-(5-isopropyl-2-methyl-1,3-thiazol-4-yl) phenoxy]pentoxy}benzamidine dimethanesulfonate and 0.2 μM alendronic acid on osteoclast differentiation, in which osteoclast differentiation was induced via co-culture of bone marrow cell and osteoblast, the cells were treated with each sample substance singly or simultaneously, and cultured for 7 days, and then TRAP staining was performed to count mature osteoclasts with 6 or more nuclei, expressed as a percentage to a control group.

FIG. 3 is a graph showing the effect of individual or combination treatment of 0.5 μM N-hydroxy-4-{5-[4-(5-isopropyl-2-methyl-1,3-thiazol-4-yl) phenoxy]pentoxy}benzamidine dimethanesulfonate and 0.2 μM alendronic acid on osteoclast differentiation, in which osteoclast differentiation was induced via co-culture of bone marrow cell and osteoblast, the cells were treated with each sample substance singly or simultaneously, and cultured for 7 days, and then TRAP staining was performed to count mature osteoclasts with 6 or more nuclei, expressed as a percentage to a control group.

DESCRIPTION OF THE PREFERRED EMBODIMENTS

In accordance with an aspect, the present invention relates to a method of treating or preventing osteoporosis, which comprises administering to a patient in need thereof an effective amount of pharmaceutical composition comprising the following compounds (a) and (b) for the purpose of using simultaneously, separately, or sequentially as active ingredients:

(a) a compound selected from N-hydroxy-4-{5-[4-(5-isopropyl-2-methyl-1,3-thiazol-4-yl)phenoxy]pentoxy}benzamidine represented by the following Formula 1, 4-{5-[4-(5-isopropyl-2-methyl-1,3-thiazol-4-yl)phenoxy]pentoxy}benzamidine represented by the following Formula 2, and salts thereof; and (b) alendronic acid represented by the following Formula 3 or a salt thereof,

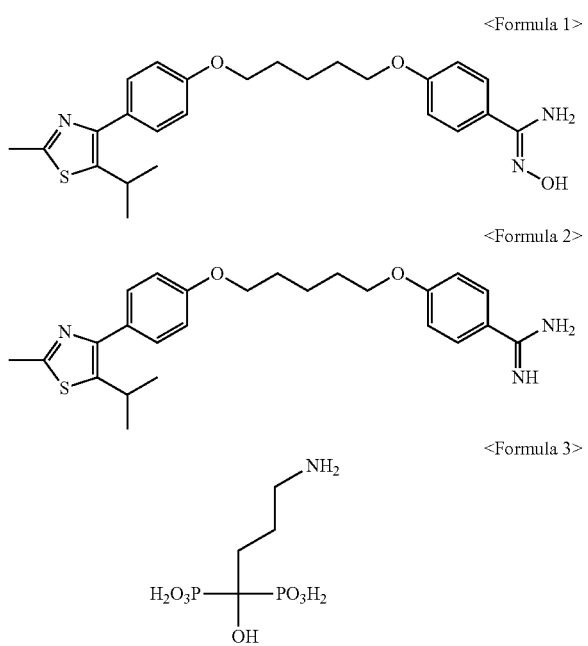

<Formula 1>
<Formula 2>
<Formula 3>

The term "osteoporosis" as used herein means the state that minerals and substrates forming the bone are reduced abnormally in large amounts, even without any defect in the structure of the remaining bone, so that many pores are generated in the bone, making it like sponge and more likely to fracture. This may be referred to as "osteopenia".

N-hydroxy-4-{5-[4-(5-isopropyl-2-methyl-1,3-thiazol-4-yl)phenoxy]pentoxy}benzamidine or 4-{5-[4-(5-isopropyl-2-methyl-1,3-thiazol-4-yl)phenoxy]pentoxy}benzamidine used in the present invention may be prepared according to known processes (Lee, Sung-Eun, *Synthesis and Biological Activity of Natural Products and Designed New Hybrid Compounds for the Treatment of LTB$_4$ Related Disease*, Busan National University, a thesis for a Ph. D degree, 1999. 8), but is not limited thereto.

On the other hand, N-hydroxy-4-{5-[4-(5-isopropyl-2-methyl-1,3-thiazol-4-yl)phenoxy]pentoxy}benzamidine or 4-{5-[4-(5-isopropyl-2-methyl-1,3-thiazol-4-yl)phenoxy]pentoxy}benzamidine may be used in the form of a pharmaceutically acceptable salt known in the art without limitation, and preferably acid addition salts prepared by a method well known in the art. As the pharmaceutically acceptable salts, inorganic acids or organic acids may be used. Examples of the inorganic acids may include hydrochloric acid, bromic acid, sulfuric acid, and phosphoric acid, and examples of the organic acids may include citric acid, acetic acid, lactic acid, tartaric acid, fumaric acid, formic acid, propionic acid, oxalic acid, trifluoroacetic acid, methane sulfonic acid, maleic acid, benzoic acid, gluconic acid, glycolic acid, succinic acid, 4-toluene sulfonic acid, galacturonic acid, embonic acid, glutamic acid, and aspartic acid. Preferably, hydrochloric acid as the inorganic acid and methane sulfonic acid as the organic acid may be used.

The dosage of N-hydroxy-4-{5-[4-(5-isopropyl-2-methyl-1,3-thiazol-4-yl)phenoxy]pentoxy}benzamidine, 4-{5-[4-(5-isopropyl-2-methyl-1,3-thiazol-4-yl)phenoxy]pentoxy}benzamidine, or salts thereof is an effective amount for the prevention or treatment of osteoporosis, and determined depending on patient's age and body weight, type of combination therapy, treatment frequency, type of desired efficacy, or administration method. In the case of using as a therapeutic or prophylactic agent, the compound may be administered in an effective amount for the treatment of osteoporosis via various routes, and its formulation, dosage or the like may be easily determined by those skilled in the art, considering administration purpose, route, and health state and body weight of a subject. In particular, N-hydroxy-4-{5-[4(5-isopropyl-2-methyl-1,3-thiazol-4-yl)phenoxy]pentoxy}benzamidine, 4-{5-[4-(5-isopropyl-2-methyl-1,3-thiazol-4-yl)phenoxy]pentoxy}benzamidine, or salts thereof may be administered in an amount of about 1 to 500 mg, and preferably 5 to 200 mg.

In addition, alendronic acid used in the present invention may be also prepared according to known processes, and a salt thereof or pharmaceutically acceptable salt thereof may be used without limitation, preferably its sodium salt. The dosage of alendronic acid or a salt thereof is an effective amount for the prevention or treatment of osteoporosis, and determined depending on patient's age and body weight, type of combination therapy, treatment frequency, type of desired efficacy, or administration method. In the case of using as a therapeutic or prophylactic agent, the compound may be administered in a typical amount. In particular, alendronic acid or a salt thereof may be administered in a daily dose of 5 to 40 mg.

In the present invention, N-hydroxy-4-{5-[4-(5-isopropyl-2-methyl-1,3-thiazol-4-yl)phenoxy]pentoxy}benzamidine, 4-{5-[4-(5-isopropyl-2-methyl-1,3-thiazol-4-yl)phenoxy]pentoxy}benzamidine, or salts thereof and alendronic acid or a salt thereof may be used in any combination thereof.

In the present invention, N-hydroxy-4-{5-[4-(5-isopropyl-2-methyl-1,3-thiazol-4-yl)phenoxy]pentoxy}benzamidine, 4-{5-[4-(5-isopropyl-2-methyl-1,3-thiazol-4-yl)phenoxy]pentoxy}benzamidine, or salts thereof and alendronic acid or a salt thereof may be simultaneously administered by mixing together, or each of them may be administered separately either simultaneously or sequentially, or may be administered separately at different times. In the case of administering separately, two active ingredients may be administered alternately or one active ingredient may be administered after completion of the administration of the other active ingredient.

In the present invention, as long as the drug comprises N-hydroxy-4{5-[4-(5-isopropyl-2-methyl-1,3-thiazol-4-yl)phenoxy]pentoxy}benzamidine, 4{5-[4-(5-isopropyl-2-methyl-1,3-thiazol-4-yl)phenoxy]pentoxy}benzamidine, or salts thereof and alendronic acid or a salt thereof as the active ingredient, it may be formulated into any pharmaceutical dosage form, for example, a combined formulation comprising two active ingredients or each single formulation. As used herein, the combined formulation means that two or more active ingredients are blended in one formulation, and the single formulation means that one active ingredient is contained in one formulation. In this connection, each of the active ingredients may be prepared into different formulation (e.g., immediate release or sustained-release form) according to its pharmacological and pharmacokinetic properties, and then may be combined with each other. In addition, the combined formulation may be formulated into a multi-layer tablet or coated tablet, where each different active ingredient is contained in each layer or coating and core. In the present invention, if two active ingredients are prepared into single formulations, the therapeutic and prophylactic agent of the present invention refers to a drug or method using the single formulations in combination thereof. Thus, each drug containing the active ingredient may be prepared into each different formulation. If two active ingredients are prepared into single formulations, two formulations may be provided in one kit.

The prophylactic or therapeutic agent for osteoporosis of the present invention may be administered, either daily or intermittently, and may be administered once or 2~3 times a day. If each of the active ingredients is a single formulation, their administration frequency may be the same as or different from each other.

N-hydroxy-4-{5-[4-(5-isopropyl-2-methyl-1,3-thiazol-4-yl)phenoxy]pentoxy}benzamidine or salts thereof and alendronic acid or a salt thereof of the present invention may be formulated alone or along with a pharmaceutically acceptable carrier or excipient by a known method. Specific examples of the formulation may include oral dosage forms such as soft capsule, hard capsule, tablet, and syrup, and injectable and topical preparations.

The pharmaceutically acceptable carrier includes any of standard pharmaceutical carriers used for the preparation of the known formulations, such as sterile liquids, tablets, coated tablets and capsules. Typically, such carriers include excipients such as such as polyvinylpyrrolidone, dextrin, starch, milk, sugar, certain types of clay, gelatin, stearic acid, talc, vegetable oils (e.g., edible oil, cotton seed oil, coconut oil, almond oil, peanut oil), liquid ester such as triglyceride, mineral oil, vassline, animal oil, cellulose derivatives (e.g., crystalline cellulose, hydroxypropylcellulose, hydroxypropylmethylcellulose, methylcellulose) and other known excipients. Such carriers may also include antioxidants, wetting agents, viscosity stabilizers, flavoring agents, coloring additives and other additives. The composition containing these carriers may be formulated by a known method.

The prophylactic and therapeutic agent for osteoporosis of the present invention means that two types of active ingredients having a different mechanism from each other, including N-hydroxy-4-{5-[4-(5-isopropyl-2-methyl-1,3-thiazol-4-yl)phenoxy]pentoxy}-benzamidine, 4-{5-[4-(5-isopropyl-2-methyl-1,3-thiazol-4-yl)phenoxy]pentoxy}-benzamidine or salts thereof and alendronic acid or a salt thereof, are used in combination, and provides excellent effects of improving bone density and strength, compared to other single drugs.

In accordance with another aspect, the present invention relates to a method for preventing or treating osteoporosis, comprising the step of administering N-hydroxy-4-{5-[4-(5-isopropyl-2-methyl-1,3-thiazol-4-yl)phenoxy]pentoxy}-benzamidine, 4-{5-[4-(5-isopropyl-2-methyl-1,3-thiazol-4-yl)phenoxy]pentoxy}-benzamidine or salts thereof and alendronic acid or a salt thereof.

As motioned above, the dosage of the compounds varies depending on various factors, and the administration route may also vary depending on various factors including patient's age, body weight, administration time period, disease severity, level of consciousness, type of combination drug. The compounds may be administered via various routes such as oral and parenteral routes, and each of the compounds may be administered separately either simultaneously or sequentially, or separately at different times.

Hereinafter, the present invention will be described in more detail with reference to Examples. However, these Examples are for illustrative purposes only, and the invention is not intended to be limited by these Examples.

For evaluation of the therapeutic effect on osteoporosis, N-hydroxy-4{5-[4(5-isopropyl-2-methyl-1,3-thiazol-4-yl)phenoxy]pentoxy}benzamidine or a salt thereof and alendronic acid or a salt thereof of the present invention were administered in combination thereof, or each of them was used as a single formulation.

The osteoclast differentiation was induced by co-culture system between bone marrow cells and carvarial cells, and inhibitory effect of the drug on osteoclast differentiation was evaluated by treatment of single or combination formulation.

EXAMPLE 1

Preparation of Bone Marrow Cells and Osteoblasts

Femora and tibia were aseptically ectomized from 6~8 week-old male ddY mice and bone marrow cells were harvested using a syringe in according to a general method. Cells were removed from the bone marrow cells, followed by centrifugation. After the bone marrow cells were suspended in α-MEM medium supplemented with 10% FBS, and the numbers of the eukaryotic cells in the harvested bone marrow cells were counted and then immediately used for a co-culture system.

The mouse calvaria were aseptically isolated from 1~2 day-old neonatal ICR mice, and the carvarial cells, primary osteoblasts were isolated by sequential treatment with an enzyme solution of 0.2% collagenase. The isolated carvarial cells was centrifuged, resuspended with α-MEM containing 10% FBS and cultured until confluent. Then, these cells were diluted to a desired cell number, and used for the experiment.

EXAMPLE 2

Measurement of Osteoclast Differentiation Via Co-Culture System

The bone marrow cells ($1 \times 10^5$ cells/well) and osteoblasts (3,000 cells/well) prepared in the above were plated in a 96-well plate using α-MEM medium supplemented with 10% FBS. At this time, differentiation factors, $1\alpha,25$-dihydroxyvitamin $D_3$ ($10^{-8}$ M, hereinbelow, referred to as vitamin $D_3$) and dexamethasone ($10^{-8}$ M), were co-added to the osteoclastic medium. The medium was replaced with fresh media containing the differentiation factors every 2 to 3 days.

After 7 days, when multinucleated osteoclasts were observed, the medium was removed from the wells, and then the cells were fixed with PBS containing 10% formalin. An index of osteoclast formation was determined by counting number of Tartrate-Resistant Acid Phosphatase—positive multinucleated osteoclasts (herein below, referred to as TRAP(+) MNCs). The TRAP staining solution was contained naphtol AS-MX phosphate(pH5.0)as a substrate, Fast Red violet LB as a coloring agent and 50 mM tartaric acid and stored at a refrigerator until use. The number of TRAP(+) MNCs containing more than 6-7 or more nuclei were counted under a microscope.

EXAMPLE 3

Effect of Test Substance on Osteoclast Differentiation

A. Preparation of Sample

N-hydroxy-4-{5-[4-(5-isopropyl-2-methyl-1,3-thiazol-4-yl)phenoxy]pentoxy}-benzamidine and 4-{5-[4-(5-isopropyl-2-methyl-1,3-thiazol-4-yl)phenoxy]pentoxy}-benzamidine of the present invention can be prepared according to known processes (Lee, Sung-Eun, *Synthesis and Biological Activity of Natural Products and Designed New Hybrid Compounds for the Treatment of $LTB_4$ Related Disease*, Busan National University, a thesis for a Ph. D degree, 1999. 8), and sodium alendronate can be also prepared according to known processes (U.S. Pat. Nos. 4,407,761, 4,621,077, 4,705,651, 5,039,819, and 5,159,108).

Individual treatment of N-hydroxy-4{5-[4-(5-isopropyl-2-methyl-1,3-thiazol-4-yl)phenoxy]pentoxy}benzamidine dimethanesulfonate or sodium alendronate, and combination treatment of N-hydroxy-4-{5-[4-(5-isopropyl-2-methyl-1,3-thiazol-4-yl)phenoxy]pentoxy}benzamidine dimethanesulfonate and sodium alendronate were performed to evaluate their effects on osteoclast differentiation by the above experiment. All experiments were performed using the osteoclastic media containing vitamin $D_3$ and dexamethasone.

N-hydroxy-4-{5-[4-(5-isopropyl-2-methyl-1,3-thiazol-4-yl)phenoxy]pentoxy}benzamidine dimethanesulfonate was dissolved in DMSO at a concentration of 0.1 mM, 0.3 mM and 0.5 mM, and then diluted 1,000 fold with the osteoclastic media to a final concentration of 0.1 μM, 0.3 μM and 0.5 μM. Sodium alendronate hydrate was dissolved in purified water at a concentration of 0.2 mM, and then diluted 1,000 fold with the osteoclastic media to a final concentration of 0.2 μM. In this connection, a control group was maintained in 0.1% DMSO. Each experiment was performed by individual or combination treatment, as follows.

EXPERIMENTAL EXAMPLE 1

Effect of Individual or Combination Treatment of 0.1 μM N-hydroxy-4-{5-[4-(5-isopropyl-2-methyl-1,3-thiazol-4-yl) phenoxyl]pentoxy}benzamidine dimethanesulfonate and 0.2 μM Sodium Alendronate on Osteoclast Differentiation A. Control (0.1% DMSO solvent)
B. Individual treatment of N-hydroxy-4-{5-[4-(5-isopropyl-2-methyl-1,3-thiazol-4-yl)phenoxy]pentoxy}benzamidine dimethanesulfonate (0.1 μM)
C. Individual treatment of sodium alendronate (0.2 μM)
D. Combination treatment of N-hydroxy-4-{5-[4-(5-isopropyl-2-methyl-1,3-thiazol-4-yl)phenoxy]pentoxy}benzamidine dimethanesulfonate (0.1 μM) and sodium alendronate (0.2 μM)

The cells, which were prepared as in the above co-culture system, were plated in each well and cultured in the presence of the sample substances or vehicle. On days 3 and 5 of culture, the media were replaced with fresh differentiation media containing the sample substances. On day 7 of culture, cells were fixed and stained for TRAP. The number of TRAP (+) MNCs with 6 or more nuclei were counted under a microscope. The results were expressed as a percentage of the relative number of mature osteoclast observed in each experimental group, when the number of mature osteoclast in the control group (solvent only) was regarded as 100%. The experiment was performed with 4 wells per experimental group (n=4), and the results were shown as mean value±standard deviation. In addition, the experiment was repeated at least twice, and Student t-test was applied for significant difference between experimental groups. The results are shown in Table 1.

As a result, the individual treatment of N-hydroxy-4-{5-[4-(5-isopropyl-2-methyl-1,3-thiazol-4-yl) phenoxy]pentoxy}benzamidine dimethanesulfonate (0.1 μM) exhibited significant reduction in the relative number of TRAP(+) MNCs compared to the control group (solvent only). The individual treatment of sodium alendronate (0.2 μM) also significantly inhibited osteoclast differentiation with the relative number of 80.6%. When the combination treatment of N-hydroxy-4-{5-[4-(5-isopropyl-2-methyl-1,3-thiazol-4-yl) phenoxy]pentoxy}benzamidine dimethanesulfonate and sodium alendronate was simultaneously performed at the above mentioned concentration, the relative number of multinucleated osteoclast was notably reduced to 36.4%, which is much lower than the sum of each individual treatment, showing the strong inhibitory effect on osteoclast differentiation. Taken together, the results demonstrate that the combination treatment of N-hydroxy-4-{5-[4-(5-isopropyl-2-methyl-1,3-thiazol-4-yl)phenoxy]pentoxy}benzamidine dimethanesulfonate and sodium alendronate exhibited much stronger efficacy than expected from the sum of each individual treatment.

EXPERIMENTAL EXAMPLE 2

Effect of Individual or Combination Treatment of 0.3 μM N-hydroxy-4-{5-[4-(5-isopropyl-2-methyl-1,3-thiazol-4-yl) phenoxy]pentoxy}benzamidine dimethanesulfonate and 0.2 μM Sodium Alendronate on Osteoclast Differentiation A. Control (0.1% DMSO solvent)
B. Individual treatment of N-hydroxy-4-{5-[4-(5-isopropyl-2-methyl-1,3-thiazol-4-yl)phenoxy]pentoxy}benzamidine dimethanesulfonate (0.3 μM)
C. Individual treatment of sodium alendronate (0.2 μM)
D. Combination treatment of N-hydroxy-4-{5-[4-(5-isopropyl-2-methyl-1,3-thiazol-4-yl)phenoxy]pentoxy}benzamidine dimethanesulfonate (0.3 μM) and sodium alendronate (0.2 μM)

The experiment was performed in the same manner as in Example 1.

Consequently, as shown in FIG. 2, in the individual treatment of N-hydroxy-4-{5-[4-(5-isopropyl-2-methyl-1,3-thiazol-4-yl) phenoxy]pentoxy}benzamidine dimethanesulfonate (0.3 μM), the relative number of osteoclast (52.4%) was found to be lower than that of the above experimental group (0.1 μM), indicating an improved inhibitory effect on osteoclast differentiation. The individual treatment of sodium alendronate significantly reduced the relative number of osteoclast, as mentioned in Example 1. When the combination treatment of two sample substances was simultaneously performed, the relative number of osteoclasts was observed to be as low as 20.1. These results demonstrate that the combination treatment of two substances exhibited much stronger efficacy than expected from the sum of each individual treatment.

EXPERIMENTAL EXAMPLE 3

Effect of Individual or Combination Treatment of 0.5 μM N-hydroxy-4-{5-[4-(5-isopropyl-2-methyl-1,3-thiazol-4-yl) phenoxy]pentoxy}benzamidine dimethanesulfonate and 0.2 μM Sodium Alendronate on Osteoclast Differentiation A. Control (0.1% DMSO solvent)
B. Individual treatment of N-hydroxy-4-{5-[4-(5-isopropyl-2-methyl-1,3-thiazol-4-yl)phenoxy]pentoxy}benzamidine dimethanesulfonate (0.5 μM)
C. Individual treatment of sodium alendronate (0.2 μM)
D. Combination treatment of N-hydroxy-4-{5-[4-(5-isopropyl-2-methyl-1,3-thiazol-4-yl)phenoxy]pentoxy}benzamidine dimethanesulfonate (0.5 μM) and sodium alendronate (0.2 μM)

The experiment was performed in the same manner as in Example 1.

As expected, the individual treatment of N-hydroxy-4-{5-[4-(5-isopropyl-2-methyl-1,3-thiazol-4-yl) phenoxy]pentoxy}benzamidine dimethanesulfonate (0.5 μM) exhibited strong inhibitory effect on osteoclast differentiation, in which the relative number of osteoclast was found to be 34.5%. When the combination treatment with 0.2 μM sodium alendronate was performed, the relative number of cell was observed to be as low as 9.7%, which is much lower than that of the control group. These results demonstrate that the combination treatment of N-hydroxy-4-{5-[4-(5-isopropyl-2-methyl-1,3-thiazol-4-yl) phenoxy]pentoxy}benzamidine dimethanesulfonate and sodium alendronate exhibited much stronger efficacy than expected from the sum of each individual treatment on osteoclast differenciation.

INDUSTRIAL APPLICABILITY

When combination treatment of N-hydroxy-4-{5-[4-(5-isopropyl-2-methyl-1,3-thiazol-4-yl)phenoxy]pentoxy}benzamidine dimethanesulfonate and sodium alendronate was simultaneously performed, much stronger inhibitory effect on osteoclast differentiation was observed than the total effect of each individual treatment. Accordingly, the combination treatment of N-hydroxy-4-{5-[4-(5-isopropyl-2-methyl-1,3-thiazol-4-yl)phenoxy]pentoxy}benzamidine, 4{5-[4-(5-isopropyl-2-methyl-1,3-thiazol-4-yl)phenoxy]pentoxy}benzamidine, or salts thereof, and alendronic acid or a salt thereof exhibits excellent inhibitory effect on bone resorption, as compared to each individual treatment, thereby providing excellent therapeutic and prophylactic effects on osteoporosis.

What is claimed is:

1. A method of treating osteoporosis, which comprises administering to a patient in need thereof an effective amount of pharmaceutical composition comprising the following compounds (a) and (b) for the purpose of using simultaneously, separately, or sequentially as active ingredients:
   (a) a compound selected from N-hydroxy-4-{5-[4-(5-isopropyl-2-methyl-1,3-thiazol-4-yl)phenoxy]pentoxy}benzamidine represented by the following Formula 1, 4-{5-[4-(5-isopropyl-2-methyl-1,3-thiazol-4-yl)phenoxy]pentoxy}benzamidine represented by the following Formula 2, and salts thereof; and
   (b) alendronic acid represented by the following Formula 3 or a salt thereof,

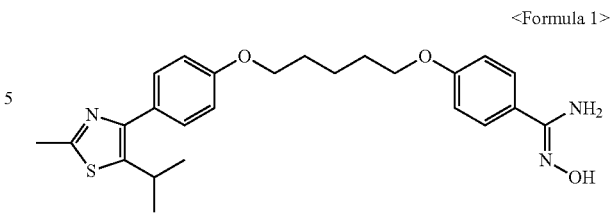

<Formula 1>

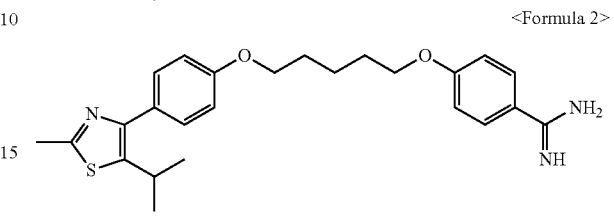

<Formula 2>

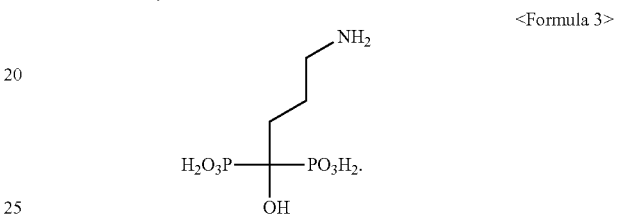

<Formula 3>

2. The method of claim 1, wherein the salt of N-hydroxy-4-{5-[4-(5-isopropyl-2-methyl-1,3-thiazol-4-yl)phenoxy]pentoxy}benzamidine or 4-{5-[4-(5-isopropyl-2-methyl-1,3-thiazol-4-yl)phenoxy]pentoxy}-benzamidine is hydrochloride or methanesulfonate.

3. The method of claim 1, wherein the salt of alendronic acid is its sodium salt.

4. The method of claim 1, wherein the pharmaceutical composition is prepared in a form of combination formulation comprising (a) and (b).

5. The method of claim 1, wherein the pharmaceutical composition is prepared in a form of single formulation comprising each of (a) and (b).

6. The method of claim 1, wherein two single formulations comprising each of (a) and (b) are provided in one kit.

* * * * *